US008986474B2

(12) United States Patent
Kufner et al.

(10) Patent No.: US 8,986,474 B2
(45) Date of Patent: Mar. 24, 2015

(54) METHOD OF MANUFACTURING A COMPOSITE SUPERABSORBENT CORE STRUCTURE

(71) Applicant: Nordson Corporation, Westlake, OH (US)

(72) Inventors: Hubert Kufner, Luneburg (DE); Ernst Hering, Barnstedt (DE)

(73) Assignee: Nordson Corporation, Westlake, OH (US)

( * ) Notice: Subject to any disclaimer, the term of this patent is extended or adjusted under 35 U.S.C. 154(b) by 165 days.

(21) Appl. No.: 13/709,258

(22) Filed: Dec. 10, 2012

(65) Prior Publication Data

US 2013/0174959 A1    Jul. 11, 2013

Related U.S. Application Data

(60) Provisional application No. 61/585,451, filed on Jan. 11, 2012.

(51) Int. Cl.
*A61F 13/539* (2006.01)
*D04H 1/56* (2006.01)
(Continued)

(52) U.S. Cl.
CPC ......... *A61F 13/15634* (2013.01); *A61F 13/539* (2013.01); *D04H 1/565* (2013.01);
(Continued)

(58) Field of Classification Search
CPC ............... A61F 13/15634; A61F 13/15642; A61F 13/1565; A61F 13/539; A61F 2013/1591; A61F 2013/530496; A61F 2013/530569; A61F 2013/530591; A61F 2013/539; A61F 2013/53908; A61L 15/60; D04H 1/565; D04H 3/16; B32B 2555/02
USPC ................. 156/62.2, 62.4, 167, 176, 276, 78; 604/365, 366, 368, 369
See application file for complete search history.

(56) References Cited

U.S. PATENT DOCUMENTS

| 4,429,001 A | * | 1/1984 | Kolpin et al. ................. 442/340 |
| 5,858,292 A | | 1/1999 | Dragoo et al. |

(Continued)

FOREIGN PATENT DOCUMENTS

| EP | 0159630 A2 | 10/1985 |
| WO | 9011181 A1 | 10/1990 |
| WO | 0032142 A1 | 6/2000 |
| WO | 03052190 A1 | 6/2003 |

OTHER PUBLICATIONS

European Patent Office, European Search Report in EP Application No. 13150236, Sep. 2, 2014.

*Primary Examiner* — Michael Tolin
(74) *Attorney, Agent, or Firm* — Wood, Herron & Evans, L.L.P.

(57) ABSTRACT

Methods related to forming superabsorbent composite core structures using superabsorbent materials, such as superabsorbent polymers (SAP). In one method superabsorbent material is sprayed simultaneously with an adhesive to form a superabsorbent layer adhered to a first flexible sheet of material. A second flexible sheet of material is applied to the superabsorbent layer to position the superabsorbent layer between the first and second flexible sheets of material. At least one of the first or second flexible sheets of material is liquid permeable to allow liquid to penetrate into the superabsorbent layer from outside the composite product.

10 Claims, 4 Drawing Sheets

(51) Int. Cl.
*D04H 3/16* (2006.01)
*A61F 13/15* (2006.01)
*A61L 15/60* (2006.01)
*A61F 13/53* (2006.01)

(52) U.S. Cl.
CPC ..... *A61F13/15642* (2013.01); *A61F 13/15658* (2013.01); *A61L 15/60* (2013.01); *A61F 2013/530496* (2013.01); *A61F 2013/530569* (2013.01); *A61F 2013/530591* (2013.01); *A61F 2013/53908* (2013.01); *A61F 2013/530554* (2013.01); *A61F 2013/1591* (2013.01); *D04H 3/16* (2013.01)
USPC ............ 156/62.4; 156/78; 156/167; 156/176; 156/276; 604/365; 604/368; 604/369

(56) References Cited

U.S. PATENT DOCUMENTS

| | | | |
|---|---|---|---|
| 5,998,493 | A | 12/1999 | Mitchell et al. |
| 6,319,342 | B1* | 11/2001 | Riddell ................. 156/62.4 |
| 6,646,180 | B1 | 11/2003 | Chmielewski |
| 6,730,387 | B2* | 5/2004 | Rezai et al. ............. 428/141 |
| 7,361,694 | B2 | 4/2008 | Strandburg et al. |
| 2003/0129915 | A1 | 7/2003 | Harriz |
| 2005/0031850 | A1 | 2/2005 | Mitchell et al. |
| 2005/0186351 | A1 | 8/2005 | Fung et al. |
| 2007/0077841 | A1 | 4/2007 | Zoch et al. |
| 2007/0197987 | A1* | 8/2007 | Tsang et al. ............. 604/365 |

\* cited by examiner

METHOD OF MANUFACTURING A COMPOSITE SUPERABSORBENT CORE STRUCTURE

CROSS-REFERENCE TO RELATED APPLICATION

This application claims the priority of U.S. Provisional Application Ser. No. 61/585,451, filed Jan. 11, 2012, the disclosure of which is hereby incorporated by reference herein.

TECHNICAL FIELD

The present invention relates to a method of manufacturing a composite superabsorbent core structure for use in disposable absorbent articles, such as personal hygienic products including diapers, incontinence pads, healthcare products and the like. More specifically, the present invention relates to methods of manufacturing composite superabsorbent core structures that include the use of superabsorbent polymers (SAP).

BACKGROUND

Disposable absorbent articles having superabsorbent core structures are well known in the art. Superabsorbent core structures traditionally have at least three functional regions, namely, an acquisition region, a distribution region, and a storage region. The design of these regions and the various materials involved can lead to manufacturing challenges and increased cost.

One conventional superabsorbent core structure includes the use of cellulosic materials. While the use of cellulosic materials provide satisfactory acquisition and distribution, often cellulosic core structures suffer from having poor storage and in addition poor wet integrity (that is, poor structural integrity when wet). Expensive binders may be used in an effort to improve the wet integrity of such cellulosic core structures. Another known problem when using cellulosic materials is the presence of knots and fines. These unsatisfactorily shaped fibers can negatively impact the core properties. The use of cellulosic materials also results in bulky core structures and can lead to undesirably thick or bulky disposable absorbent articles.

Another conventional superabsorbent core structure includes the use of synthetic meltblown fibers. While the use of synthetic meltblown fibers provides satisfactory wet integrity, the resulting core structure can have poor acquisition properties. Further, these meltblown fibers are small and tend to be weak, leading to undesirable core properties. Additionally, synthetic meltblown core structures often require the use of expensive binders.

Conventional superabsorbent core structures for use in disposable absorbent articles may be composite structures, i.e., structures that are made of discrete, multiple layers of materials, including layers of different types of materials. For example, a conventional absorbent core structure may be made of: (a) a top layer which serves as an acquisition region for more immediate absorption of exudate from the wearer, (b) an intermediate layer which serves as a distribution region for the intended transportation of exudate within the superabsorbent core structure and (c) a bottom layer which serves as a storage region for longer term storage of exudate. One of the materials that has been used in the core structure, and especially the bottom layer or storage region, is SAP. This material has been incorporated in various manners, such as by being blown into the bottom layer during manufacture.

Another method of using SAP has been to include the SAP directly in an adhesive. In this situation, the adhesive is used as a carrier for the SAP. The adhesive is then applied to a substrate in areas in which the substantial liquid absorption properties of SAP are desired. Challenges are associated with known ways of combining SAP and adhesive. For example, the adhesive restricts the necessary expansion of the SAP and, therefore, inhibit liquid absorption rates of the SAP. The total liquid holding capacity of the SAP is also reduced because of the entrapment of the SAP within the adhesive. Also, liquid cannot permeate through or past the adhesive in order to contact the SAP. This presents difficulties with respect to arriving at manufacturing processes related to adhesives containing SAP.

It would be desirable to provide a superabsorbent composite core structure that can eliminate or at least reduce problems such as those described above.

SUMMARY

Generally, the invention is a method of forming a composite superabsorbent core structure. The method includes spraying a first plurality of adhesive filaments toward a first flexible sheet of material, the filaments having an average diameter. Particles of superabsorbent particulate material are sprayed toward the first flexible sheet of material and the particles also have an average diameter. The average diameter of the particles of superabsorbent material is greater than the average diameter of the filaments. The filaments and the particles are mixed in the air such that the filaments partially coat the particles while leaving surface area portions of the particles uncoated. The partially coated particles and the adhesive are applied to the first flexible sheet of material to form a superabsorbent layer. A second flexible sheet of material is applied directly or indirectly to the superabsorbent layer to position the superabsorbent layer between the first and second flexible sheets of material. At least one of the first or second flexible sheets of material is liquid permeable to allow liquid to penetrate into the superabsorbent layer, contact the uncoated surface area portions and become absorbed by the superabsorbent particulate material.

Additional aspects of the method are provided in various embodiments. A preferred embodiment includes spraying the plurality of adhesive filaments as a generally aligned or linear array toward the first flexible sheet of material. For example, this is accomplished by using a plurality of valve modules attached to a manifold. The adhesive may be a foamed adhesive that forms an open cell structure potentially allowing liquid to better travel through and within the superabsorbent layer so as to contact and be absorbed by the superabsorbent material. In addition, the use of a foamed adhesive may better allow for expansion of the superabsorbent material as the liquid is absorbed. However, the adhesive may instead be unfoamed adhesive sprayed in filament form creating a network of adhesive filaments that partially coats the particles of superabsorbent material. The partial coating of the superabsorbent particles with the foamed or unfoamed adhesive allows liquid permeation of the superabsorbent material after application. The liquid permeable sheet or sheets can further comprise nonwoven material such as those commonly used in the construction of personal hygienic products. The superabsorbent material used in this method is a powder form of superabsorbent polymer (SAP) that is scattered or dispersed with a suitable device. For example, the device may gravity feed the powder to a scattering element or the powder may be sprayed with the assistance of pressurized air. Other superabsorbent particulate materials may be used instead, including non-polymeric materials.

In another embodiment, the mixture of adhesive and superabsorbent material occurs between two converging adhesive filament streams. It will be understood that one or more additional layers of sheet or other material may be positioned between the superabsorbent layer and the second sheet of material and, in such a case, the second sheet is indirectly applied to the superabsorbent layer. In another embodiment, the liquid permeable sheet receives the adhesive and superabsorbent material combination and is folded over later in the process to contain the mixture. In this case, a second sheet of material is applied indirectly to the resulting superabsorbent layer by, for example, being applied to one of the folded over sheet portions. Disposable hygienic products may be manufactured using the superabsorbent core structures of the invention. Examples of such products are diapers, incontinence pads, bed pads and other healthcare products. The various other features discussed herein are also applicable to this embodiment and may be used in any desired combination.

Various additional advantages and features will become more readily apparent to those of ordinary skill in the art upon review of the following detailed description of the illustrative embodiments taken in conjunction with the accompanying drawings.

DETAILED DESCRIPTION OF THE
ILLUSTRATIVE EMBODIMENTS

It should be noted that, when employed herein the term "particle" or "particulate" and the like, when used with the term "superabsorbent" or superabsorbent polymer" general encompasses any discrete shape or form. The particles or particulates can comprise flakes, fibers, agglomerates, granules, spheres, or the like, as well as combinations thereof. The particles or particulates can have any desired shape such as, for example, polygonal, rod-like, polyhedral, spherical or other rounded or angular shapes of regular or irregular forms. The terms "particle" and "particulate" are also inclusive of an agglomeration comprising more than one individual particle. Additionally, a particle or particulate may comprise more than one type of material.

The term "superabsorbent," when used alone or in connection with polymeric or non-polymeric materials, refers to water-swellable, water-insoluble organic or inorganic materials capable, under the most favorable conditions, of absorbing at least about 10 times its weight in an aqueous solution containing 0.9 weight percent sodium chloride.

Figure 1:
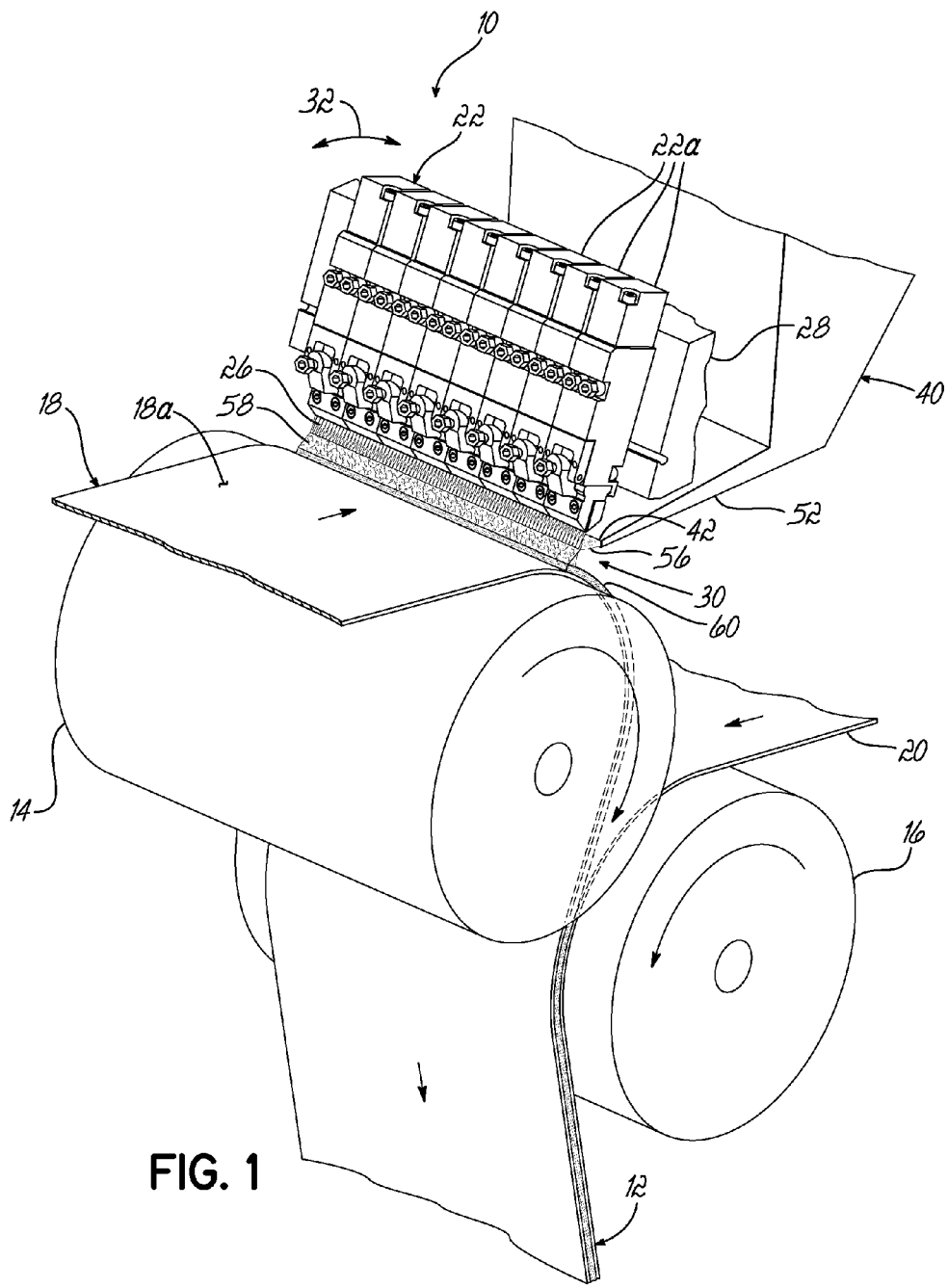
FIG. 1 is a schematic perspective view of a manufacturing system for constructing a composite, superabsorbent core structure in accordance with an illustrative embodiment.
Figure 2:
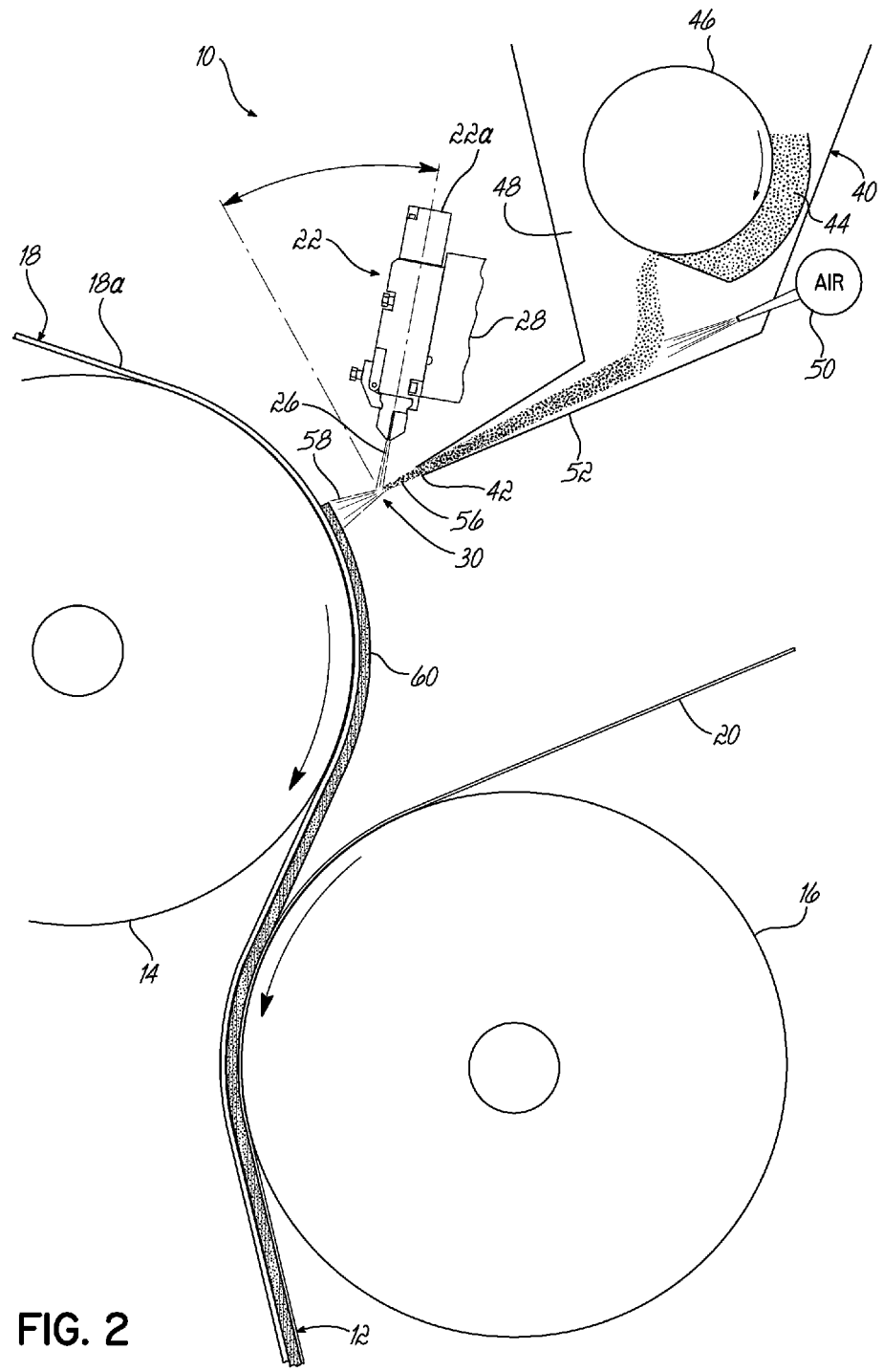
FIG. 2 is a schematic side view of the system shown in FIG. 1.

FIGS. 1 and 2 illustrate a first embodiment of a manufacturing system 10 and method for forming a superabsorbent composite core structure 12. It will be understood that this system will generally be just a part of an overall manufacturing system and, for example, will typically include additional upstream and/or downstream operations designed to manufacture a disposable absorbent end product, such as a personal hygienic product or other absorbent products, such as bed pads, etc. As examples, these would include diapers, incontinence pads and the like. Many other types of disposable absorbent products may also be manufactured using a composite superabsorbent core structure formed as generally described herein.

First and second rollers 14, 16 receive respective first and second flexible sheets 18, 20 of material, shown as continuous webs of material. For purposes of making personal hygienic products, one of the sheets of material may be a backsheet, such as polyethylene, which is liquid impervious, while the other sheet may be liquid permeable and formed, for example, from a nonwoven material. An adhesive spray dispensing unit 22 is adjustably mounted adjacent to the first sheet 18 carried by the roller 14 and sprays hot melt adhesive 26 generally toward the outwardly facing surface 18a of the moving sheet 18. In this example, a single adhesive dispensing unit 22 comprises multiple adhesive valve modules 22a that together effectively spray a generally aligned or linear array of adhesive filaments 26 to an area 30 spaced from the surface 18a. The valve modules 22a are mounted to one or more heated manifolds 28 for purposes of supplying hot melt adhesive and process air for attenuating the adhesive filaments comprising the array 26. The angle of the unit 22 may be adjusted as shown by arrow 32. The individual filament pattern may take many different forms, including swirls or other filament patterns. Suitable adhesive applicators or valve modules 22a are those sold by Nordson Corporation including the Signature® nozzle, such as shown and described in U.S. Patent Publication No. 2009/0258138 or U.S. Pat. No. 7,798,434, the disclosures of which are hereby fully incorporated by reference herein. The valve modules 22a may be of the type shown and described in U.S. Pat. No. 6,676,038, the disclosure of which is hereby fully incorporated by reference herein.

A powder discharging unit 40 is also mounted such that an outlet 42 of the unit 40 is directed at the area 30 which receives the adhesive 26. The powder discharge unit 40 includes a supply of SAP powder 44 (FIG. 2) that is appropriately metered such as by a metering wheel 46 into a receiving chamber 48. Pressurized air from a source 50 is directed into a discharge outlet passage 52 to intermix with the SAP powder forming an elongate stream of air and powder mixture 56 that intermixes with the adhesive 26. Alternatively, the powder 44 may be scattered or dispersed into the adhesive 26 with any other suitable device. As will be shown and described further in connection with FIG. 4, particles of the SAP powder 44 will be partially but not fully coated with adhesive 26 as the SAP 44 and adhesive 26 contact one another in the air. The particles remain partially coated after the mixture is applied to the sheet 18. It will be appreciated that some particles of the SAP powder might remain uncoated or even fully coated, but it is preferred that a majority of the particles are only partially coated as described further below with reference to FIG. 4. The partial coating of the particles allows the particles to be bound to one another and also adhere to the sheet 18, while maintaining the ability of moisture to directly contact the uncoated areas of the particles for direct absorption. In addition, the partial coating allows fuller expansion of the particles as the moisture is absorbed. The mixture 56 has a width approximately equal to the length of the dispenser 22, which is dependent on the number of modules 22a. The width of the mixture 56 is approximately equal to or less than the width of the sheet 18. The adhesive 26 and SAP powder 44 mix together in the air (i.e., area 30) prior to contacting and adhering to the sheet 18 of material. The adhesive 26 and powder 44 bind together as an entangled or intermingled network forming an airborne mixture 58 of adhesive and SAP which is then applied to the sheet 18 of material. This forms a superabsorbent layer 60 of the intermingled SAP 44 and sprayed liquid adhesive 26 on the surface 18a of the first sheet 18. These first and second layers 18, 60 of the core structure 12 are then adhered to a third layer, e.g., the second flexible sheet 20 moving on the roller 16. The three layer composite core structure 12 is then moved downstream from the roller 16 for any subsequent manufacturing processing, such as for purposes of making a disposable personal hygienic product. It will be appreciated that additional layers of sheet material or other material may be applied to the superabsorbent layer 60 before or after the second sheet 20 is applied. As another option, not shown, the first flexible sheet 18 may be folded over to contain the superabsorbent layer 60 prior to application of the second flexible sheet 20 and/or other layers thereto.

The SAP material 44 used in the embodiments of this invention may, for example, comprise powder forms of SAP in which the individual SAP particles have a size ranging from about 30 microns to about 150 microns. The adhesive is sprayed in forms that include filaments discharged and attenuated to a filament diameter ranging from about 10 microns to about 20 microns. The adhesive filament diameter size may be adjusted in various manners, such as by adjusting the flow rate and/or pressure of process air that is used to attenuate the filaments as they discharge from the nozzle of each module 22a. As other options, the diameter of the adhesive outlet associated with the module 22a may be changed, the adhesive temperature may be changed and/or the distance between the module 22a and the sheet 18 may be adjusted. The average diameter of the adhesive filaments is less than the average diameter of the SAP particles. The mixture 58 of SAP and adhesive is applied to the first substrate 18 in a thickness suitable for the intended application. For example, a smaller sized diaper may require a layer 60 having a thickness of about 2 mm to about 3 mm, whereas an adult sized product may have a layer 60 with a thickness of about 4 mm to about 5 mm. The difference in thickness will typically be adjusted by adjusting the amount of adhesive and SAP mixture 58 applied to the first sheet 18, as opposed to adjusting the particle size of the SAP, for example. The adhesive may be foamed or solid adhesive. The use of foamed adhesive will result in lower overall costs since the amount of adhesive will be lowered by as much as about 50 percent.

Figure 3:
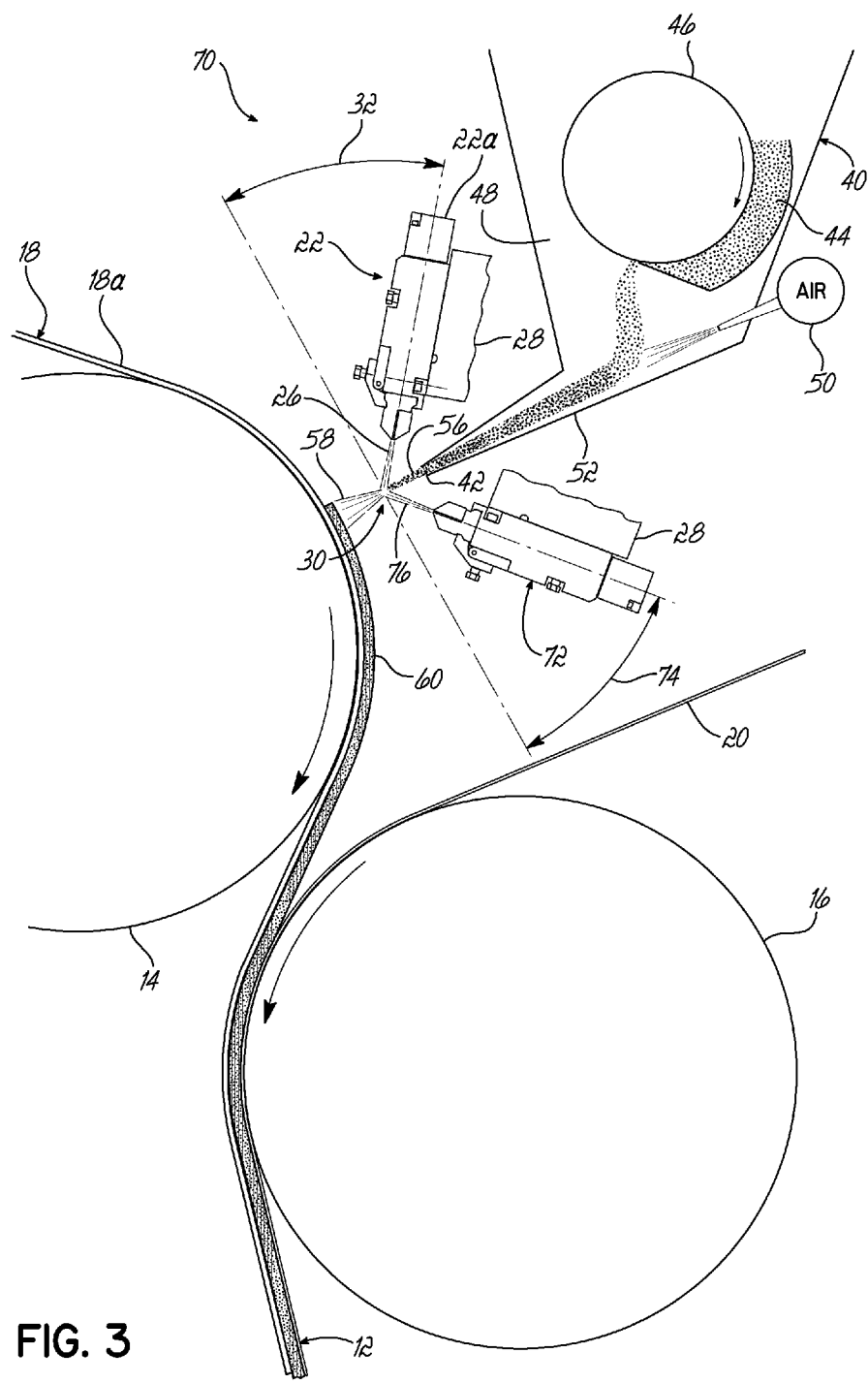
FIG. 3 is an illustration similar to FIG. 2, but showing an alternative system with two adhesive dispensing units.

FIG. 3 illustrates another alternative system 70 constructed in accordance with an embodiment of the invention. This system 70 is similar to the system 10 shown in FIGS. 1 and 2, except that a second adhesive dispensing unit 72 is mounted adjacent to the powder discharge unit 40 and on an opposite side of the stream 56 of discharged powder 44 and the area 30. Like the first dispensing unit 22, this second dispensing unit 72 may also be adjustable as indicated by arrow 74 such that the angle of convergence between the first and second discharged streams 26, 76 of adhesive may be changed to optimize the intermingling and mixing of the adhesive and SAP powder in the area 30 in which intermingling takes place. The second adhesive dispensing unit 72 is of the same design as the first adhesive dispensing unit 22. All other aspects of the system 70 shown in FIG. 3 are the same as shown and described in connection with the system 10 of FIGS. 1 and 2 and, therefore, like reference numerals are used on like elements in these drawings and no further description is necessary.

Figure 4:
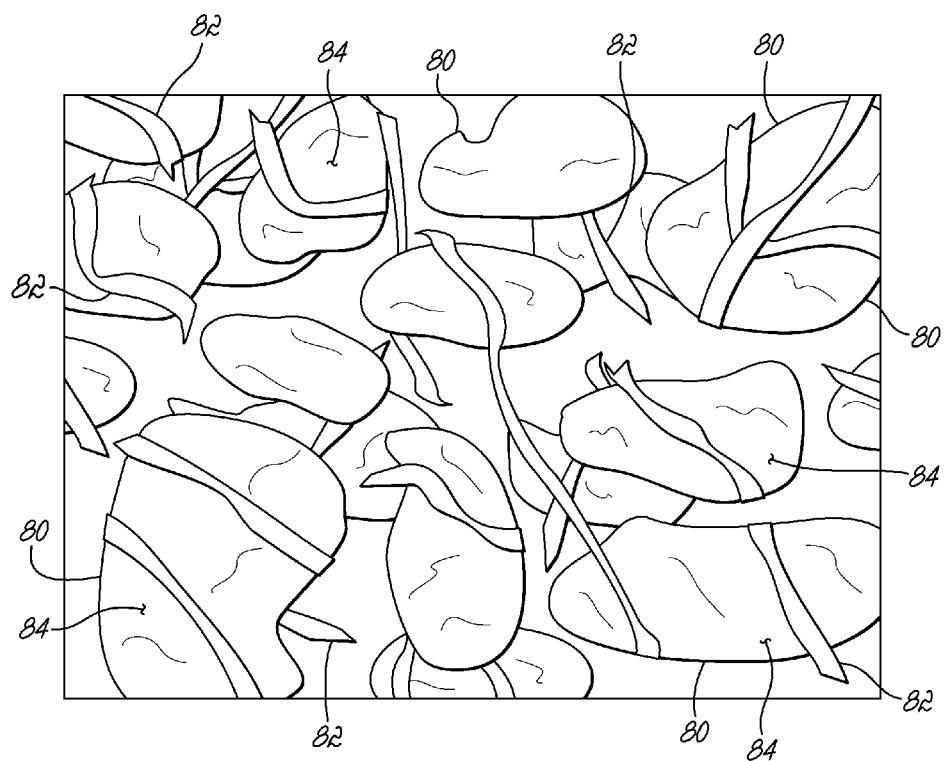
FIG. 4 is a greatly magnified, schematic illustration of a mixture of superabsorbent powder or particulate material and adhesive filaments formed with the systems of FIGS. 1-3.

FIG. 4 is a greatly enlarged and schematic view of SAP particles 80 intermingled or mixed with adhesive filaments 82. This schematic view illustrates one preferred manner of entangling and partially coating the SAP particles 80 with the adhesive filaments 82 in such a manner that the mixture 58 of intermingled adhesive and SAP particles (see FIGS. 1-3) may be effectively adhered to the first sheet 18. Additionally, the SAP particles 80 are effective to absorb liquid in the composite core structure 12. As shown in FIG. 4, the adhesive filaments 82 adhere to the particles 80, but surface areas 84 of particles 80 remain exposed or uncoated with adhesive filaments 82 such that surface areas 84 of particles 80 will still come into direct contact with liquid during use of the core structure 12. In this manner, the liquid is effectively absorbed by the particles 80 and expansion of the SAP particles 80 can better take place.

While the present invention has been illustrated by a description of various preferred embodiments and while these embodiments have been described in some detail, it is not the intention of the Applicants to restrict or in any way limit the scope of the appended claims to such detail. Additional advantages and modifications will readily appear to those skilled in the art. The various features of the invention may be used alone or in any combination depending on the needs and preferences of the user. This has been a description of the present invention, along with the preferred methods of practicing the present invention as currently known. However, the invention itself should only be defined by the appended claims.

What is claimed is:

1. A method of forming a composite superabsorbent core structure, comprising:
   spraying a first plurality of foamed adhesive filaments toward a first flexible sheet of material, the filaments having an average diameter;
   spraying particles of a superabsorbent particulate material toward the first flexible sheet of material, the particles having an average diameter greater than the average diameter of the filaments;
   mixing the filaments and the particles in an area spaced from the first flexible sheet of material such that the filaments partially coat the particles while leaving surface area portions of the particles uncoated;
   applying the partially coated particles and adhesive to the first flexible sheet of material to form a superabsorbent layer; and
   applying a second flexible sheet of material directly or indirectly to the superabsorbent layer to position the superabsorbent layer between the first and second flexible sheets of material, wherein at least one of the first or second flexible sheets of material is liquid permeable to allow liquid to penetrate into the superabsorbent layer, contact the uncoated surface area portions and become absorbed by the superabsorbent particulate material.

2. The method of claim 1, wherein the liquid permeable sheet or sheets further comprise a nonwoven material.

3. The method of claim 1, further comprising:
   manufacturing a disposable hygienic product using the superabsorbent core structure.

4. The method of claim 1, wherein the spraying the superabsorbent particulate material further comprises spraying a powder form of SAP.

5. The method of claim 1, wherein one of the first or second sheets is liquid impervious.

6. The method of claim 1, further comprising:
   spraying a second plurality of adhesive filaments toward the first flexible sheet of material, the second plurality of adhesive filaments comprised of filaments having an average diameter less than the average diameter of the particles; and mixing the adhesive filaments from the first and second pluralities of adhesive filaments with the particles to partially coat the particles while leaving surface area portions of the particles uncoated.

7. The method of claim 6, wherein spraying the first and second pluralities of adhesive filaments further comprises:

spraying the first and second pluralities of adhesive filaments in first and second generally linear arrays.

8. The method of claim 7, further comprising:

spraying the first and second pluralities of adhesive filaments in a converging manner toward the particles of superabsorbent particulate material.

9. The method of claim 8, wherein spraying the second plurality of adhesive filaments further comprises spraying foamed adhesive filaments.

10. The method of claim 6, wherein spraying the second plurality of adhesive filaments further comprises spraying foamed adhesive filaments.

* * * * *